(12) United States Patent
Modi

(10) Patent No.: US 6,436,367 B1
(45) Date of Patent: *Aug. 20, 2002

(54) AEROSOL FORMULATIONS FOR BUCCAL AND PULMONARY APPLICATION

(75) Inventor: Pankaj Modi, Ancaster (CA)

(73) Assignee: Generex Pharmaceuticals Inc., Toronto (CA)

(*) Notice: Subject to any disclaimer, the term of this patent is extended or adjusted under 35 U.S.C. 154(b) by 0 days.

This patent is subject to a terminal disclaimer.

(21) Appl. No.: 09/251,464

(22) Filed: Feb. 17, 1999

Related U.S. Application Data

(60) Provisional application No. 60/113,239, filed on Dec. 21, 1998.

(51) Int. Cl.$^7$ .......................... A61K 9/00; A61K 31/00; A61K 38/00; A61K 47/00; A61W 39/00

(52) U.S. Cl. .......................... 424/45; 424/43; 424/85.1; 424/85.2; 424/85.4; 424/130.1; 424/184.1; 424/278.1; 424/450; 514/2; 514/3; 514/4; 514/8; 514/44; 514/169; 514/282; 514/731; 514/772; 514/773; 514/783; 514/784; 514/785; 514/808; 514/822; 514/937; 514/957; 514/958; 514/970; 514/974; 514/975

(58) Field of Search ............... 514/3, 4, 946, 514/947, 957, 975, 2, 8, 44, 169, 282, 731, 772, 773, 783, 784, 785, 808, 822, 937, 958, 970, 974; 424/43, 45, 450, 85.1, 85.2, 85.4, 130.1, 184.1, 278.1

(56) References Cited

U.S. PATENT DOCUMENTS

| | | | |
|---|---|---|---|
| 4,614,730 A | 9/1986 | Hansen et al. .................. 514/3 |
| 4,900,730 A | 2/1990 | Miyauchi ...................... 514/12 |
| 5,230,884 A | 7/1993 | Evans et al. ................... 424/45 |
| 5,292,499 A | 3/1994 | Evans et al. ................... 424/45 |
| 5,376,646 A | 12/1994 | Pittrof et al. ................. 514/78 |
| 5,514,670 A | 5/1996 | Friedman et al. ............... 514/2 |
| 5,591,713 A | 1/1997 | Igari et al. ...................... 514/8 |
| 5,665,700 A | 9/1997 | Cho et al. ....................... 514/2 |
| 5,690,954 A | 11/1997 | Illum .......................... 424/434 |
| 5,747,445 A * | 5/1998 | Backstrom et al. ............. 514/4 |
| 6,017,545 A * | 1/2000 | Modi ........................... 424/400 |

FOREIGN PATENT DOCUMENTS

| | | |
|---|---|---|
| EP | 0200383 | 12/1986 |
| EP | 0272097 | 6/1988 |
| WO | 96/36352 | * 11/1996 |

OTHER PUBLICATIONS

Remington's Pharmaceutical Sciences (17th Ed. 1985), pp. 293–297, 1662–1677.*

* cited by examiner

Primary Examiner—Jose' G. Dees
Assistant Examiner—Frank Choi
(74) Attorney, Agent, or Firm—Debra Z. Anderson; Eckert Seamans Cherin & Mellott, LLC

(57) ABSTRACT

A mixed micellar aerosol pharmaceutical formulation includes a micellar proteinic pharmaceutical agent, an alkali metal lauryl sulphate, at least three micelle forming compounds, a phenol and a propellant. The micelle forming compounds are selected from the group consisting of lecithin, hyaluronic acid, pharmaceutically acceptable salts of hyaluronic acid, glycolic acid, lactic acid, chamomile extract, cucumber extract, oleic acid, linoleic acid, linolenic acid, monoolein, monooleates, monolaurates, borage oil, evening of primrose oil, menthol, trihydroxy oxo cholanyl glycine and pharmaceutically acceptable salts thereof, glycerin, polyglycerin, lysine, polylysine, triolein, polyoxyethylene ethers and analogues thereof, polidocanol alkyl ethers and analogues thereof. The amount of each micelle forming compound is present in a concentration of from 1 to 20 wt./wt. % of the total formulation, and the total concentration of micelle forming compounds are less than 50 wt./wt. % of the formulation. The propellant, e.g. a fluorocarbon propellant, provides enhanced absorption of the pharmaceutical agent.

20 Claims, No Drawings

AEROSOL FORMULATIONS FOR BUCCAL AND PULMONARY APPLICATION

This application is a continuation of provisional application No. 60/113,239 filed Dec. 21, 1998.

FIELD OF THE INVENTION

The present invention relates to an improved delivery system for the administration of large-molecule pharmaceuticals, e.g. peptidic drugs, vaccines and hormones. In particular it relates to pharmaceuticals which may be administered by means of an aerosol into the mouth, for buccal or pulmonary application.

BACKGROUND TO THE INVENTION

In spite of significant efforts in academic and commercial laboratories, major breakthroughs in oral peptide and protein formulation have not been achieved. Relatively little progress has been made in reaching the target of safe and effective oral formulations for peptides and proteins. The major barriers to developing oral formulations for proteins and peptides include poor intrinsic permeability, lumenal and cellular enzymatic degradation, rapid clearance, and chemical stability in the gastrointestinal (GI) tract. Pharmaceutical approaches to address these barriers, which have been successful with traditional small, organic drug molecules, have not readily translated into effective peptide and protein formulations. Although the challenges are significant, the potential therapeutic benefits remain high especially in the field of diabetes treatment using insulin.

Scientists have explored various administration routes other than the injection for proteins and peptides. Oral and nasal cavities have been of greatest interest to scientists. Both the oral and nasal membranes offer advantages over other routes of administration. For example, drugs administered through these membranes have a rapid onset of action, provide therapeutic plasma levels, avoid first pass effect of hepatic metabolism, and avoid exposure of the drug to hostile GI environment. Additional advantages include easy access to the membrane sites so that the drug can be applied, localized and removed easily. Further, there is a good potential for prolonged delivery of large molecules through these membranes.

The oral routes have received far more attention than has the other routes. The sublingual mucosa includes the membrane of ventral surface of the tongue and the floor of the mouth whereas the buccal mucosa constitutes the lining of the cheek. The sublingual mucosa is relatively permeable thus giving rapid absorption and acceptable bioavailability of many drugs. Further, the sublingual mucosa is convenient, acceptable and easily accessible. This route has been investigated clinically for the delivery of a substantial number of drugs.

The ability of molecules to permeate through the oral mucosa appears to be related to molecular size, lipid solubility and peptide protein ionization. Small molecules, less than 1000 daltons appear to cross mucosa rapidly. As molecular size increases, the permeability decreases rapidly. Lipid soluble compounds are more permeable than non-lipid soluble molecules. Maximum absorption occurs when molecules are un-ionized or neutral in electrical charges. Therefore charged molecules present the biggest challenges to absorption through the oral mucosae.

Most proteinic drug molecules are extremely large molecules with molecular weight exceeding 6000 daltons. These large molecules have very poor lipid solubility and are practically impermeable. Substances that facilitate the absorption or transport of large molecules (>2000 daltons) across biological membranes are known as enhancers, (Lee et al., Critical Reviews in Therapeutic drug Carrier Systems, 8, 91, 1991; Lee et al., Critical Reviews in Therapeutic drug Carrier Systems, 8, 115, 1991, 1992). Enhancers have been characterized as chelators, bile salts, fatty acids, synthetic hydrophilic and hydrophobic compounds, and biodegradable polymeric compounds.

Various mechanisms of action of enhancers have been proposed. These mechanisms of action, at least for protein and peptidic drugs include (1) reducing viscosity and/or elasticity of mucous layer, (2) facilitating transcellular transport by increasing the fluidity of the lipid bilayer of membranes, and (3) increasing the thermodynamic activity of drugs (Critical Rev, 117–125, 1991, 1992).

Many enhancers have been tested so far and some have found to be effective in facilitating mucosal administration of large molecule drugs. However, hardly any penetration enhancing products have reached the market place. Reasons for this include lack of a satisfactory safety profile respecting irritation, lowering of the barrier function, and impairment of the mucocilliary clearance protective mechanism. It has been found that some enhancers, especially those related to bile salts, and some protein solubilizing agents give an extremely bitter and unpleasant taste. This makes their use almost impossible for human consumption on a daily basis. Several approaches have been utilized to improve the taste of the bile salts based delivery systems, but none one of them are commercially acceptable for human oral consumption to date. Among the approaches utilized includes patches for buccal mucosa, bilayer tablets, controlled release tablets, use of protease inhibitors, buccally administered film patch devices, and various polymer matrices.

The basic problem associated with the above technologies is the use of large quantities of bile acids and their salts to promote the transport of the large molecules through membranes in the form of localized delivery system using patches or tablets. In spite of using protease inhibitors and polymer coatings the technologies failed to deliver proteinic drugs in the required therapeutic concentrations. Further, the problem is compounded because of the localized site effect of the patch which resulted in severe tissue damage in the mouth. Most attempts were made to deliver large molecules via the oral, nasal, rectal, and vaginal routes using single bile acids or enhancing agents in combination with protease inhibitors and biodegradable polymeric materials. However, it is extremely difficult to achieve therapeutic levels of proteinic drugs using these formulations. Single enhancing agents fail to loosen tight cellular junctions in the oral, nasal, rectal and vaginal cavities for a required period of time in order to permit passage of large molecules through the mucosal membranes without further degradation. This problem makes it impractical to use the above mentioned systems commercially.

Oral delivery offers a variety of benefits for systemic drug delivery. For example, it provides easy, non-invasive access to a permeable mucosa, which facilitates rapid drug absorption and a fast onset of action of the drug. In comparison to the GI tract and other organs, the buccal environment has lower enzymatic activity and a neutral pH.

In order to overcome the above mentioned problem of the bitter taste, irritation and the penetration of large molecules through the sublingual, buccal and GI tract mucosal lining, a system has now been designed where a proteinic drug is encapsulated in mixed micelles made up of a combination of enhancers.

A method of substantially overcoming the above disadvantages has now been found. The amount of physiologically peptide or protein in the compositions of the present invention is typically a quantity that provides an effective amount of the pharmaceutical or drug to produce the physiological activity (therapeutic plasma level) for which peptide or protein is being administered. In consideration of the fact that the bioavailability of any active substance can never be 100%, it is preferable to incorporate slightly larger amount than the desired dosage. It is believed that improvements in penetration and absorption of mixed micellar formulations can be achieved by administering the mixed micellar formulation with propellants such as tetrafluoroethane, heptafluoroethane, dimethylfluoropropane, tetrafluoropropane, butane, isobutane, dimethyl ether and other non-CFC and CFC propellants. Preferably they are delivered through metered dose spray devices. Metered dose inhalers are known and are a popular pulmonary drug delivery form for some drugs. The present formulation, including the propellant, is intended to improve the quality of absorption, stability and performance of many formulations. The compositions have been selected to give enhancement in the penetration through pores, and facilitate absorption of the drugs to reach therapeutic levels in the plasma.

One of the other benefits of using an atomizer or inhaler is that the potential for contamination is minimized because the devices are self contained.

SUMMARY OF THE INVENTION

Accordingly the present invention provides a mixed micellar aerosol pharmaceutical formulation and a propellant, comprising i) a proteinic pharmaceutical agent in micellar form, ii) water, iii) an alkali metal C8 to C22 alkyl sulphate in a concentration of from 1 to 20 wt./wt. % of the total formulation, iv) at least three micelle forming compounds selected from the group consisting of lecithin, hyaluronic acid, pharmaceutically acceptable salts of hyaluronic acid, glycolic acid, lactic acid, chamomile extract, cucumber extract, oleic acid, linoleic acid, linolenic acid, monoolein, monooleates, monolaurates, borage oil, evening of primrose oil, menthol, trihydroxy oxo cholanylglycine and pharmaceutically acceptable salts thereof, glycerin, polyglycerin, lysine, polylysine, triolein, polyoxyethylene ethers and analogues thereof, polidocanol alkyl ethers and analogues thereof, and mixtures thereof, wherein the amount of each micelle forming compound is present in a concentration of from 1 to 20 wt./wt. % of the total formulation, and the total concentration of micelle forming compounds are less than 50 wt./wt. % of the formulation, v) a phenolic compound selected from the group consisting of phenol and methyl phenol in a concentration of from 1 to 10 wt./wt. % of the total formulation, and vi) a propellant selected from the group consisting of C1–C2 dialkyl ether, butanes, fluorocarbon propellant, hydrogen-containing fluorocarbon propellant, chlorofluorocarbon propellant, hydrogen-containing chlorofluorocarbon propellant, and mixtures thereof.

In one embodiment, the alkali metal C8 to C22 alkyl sulphate is in a concentration of from 2 to 5 wt./wt. % of the total formulation.

In another embodiment, the alkali metal C8 to C22 alkyl sulphate is sodium lauryl sulphate.

In another embodiment, the lecithin is saturated or unsaturated, preferably selected from the group consisting of phosphatidylcholine, phosphatidyl serine, sphingomyelin, phosphatidylethanolamine, cephalin, and lysolecithin.

In yet another embodiment, at least one of the micelle forming compounds is selected from the group consisting of hyaluronic acid, pharmaceutically acceptable salts of hyaluronic acid, polidocanol alkyl ethers, trihydroxy oxo cholanyl glycine, polyoxyethylene ethers, triolein and mixtures thereof, the concentration such micelle forming compound being from about 1 to about 5 wt./wt. %.

Preferably, the ratio of proteinic pharmaceutical agent, e.g. insulin, to propellant is from 5:95 to 25:75.

In another embodiment, the propellant is selected from the group consisting of tetrafluoroethane, tetrafluoropropane, dimethylfluoropropane, heptafluoropropane, dimethyl ether, n-butane and isobutane.

In yet another embodiment, the mixed micellar pharmaceutical formulation and propellant are contained in an aerosol dispenser.

For insulin-containing and some other compositions, the composition may also contains at least one inorganic salt which opens channels in the gastrointestinal tract and may provide additional stimulation to release insulin. Non-limiting examples of inorganic salts are sodium, potassium, calcium and zinc salts, especially sodium chloride, potassium chloride, calcium chloride, zinc chloride and sodium bicarbonate.

It will be recognized by those skilled in the art that for many pharmaceutical compositions it is usual to add at least one antioxidant to prevent degradation and oxidation of the pharmaceutically active ingredients. It will also be understood by those skilled in the art that colorants, flavouring agents and non-therapeutic amounts of other compounds may be included in the formulation. Typical flavouring agents are menthol, sorbitol and fruit flavours.

In one embodiment the antioxidant is selected from the group consisting of tocopherol, deteroxime mesylate, methyl paraben, ethyl paraben, ascorbic acid and mixtures thereof. A preferred antioxidant is tocopherol.

In a preferred embodiment at least one protease inhibitor is added to the formulation to inhibit degradation of the pharmaceutical agent by the action of proteolytic enzymes. Of the known protease inhibitors, most are effective at concentrations of from 1 to 3 wt./wt. % of the formulation.

Non-limiting examples of effective protease inhibitors are bacitracin, soyabean trypsin, aprotinin and bacitracin derivatives, e.g. bacitracin methylene disalicylate. Bacitracin is the most effective of those named when used in concentrations of from 1.5 to 2 wt./wt. %. Soyabean trypsin and aprotinin also may be used in concentrations of about 1 to 2 wt./wt. % of the formulation.

The proteinic pharmaceutical agent may be selected from a wide variety of macromolecular agents, depending on the disorder to be treated, generally with molecular weights greater than about 1000 and especially between about 1000 and 2,000,000. Preferred pharmaceutical agents are selected from the group consisting of insulin, heparin, low molecular weight heparin, hirulog, hirugen, huridine, interferons, interleukins, cytokines, mono and polyclonal antibodies, immunoglobins, chemotherapeutic agents, vaccines, glycoproteins, bacterial toxoids, hormones, calcitonins, insulin like growth factors (IGF), glucagon like peptides (GLP-1), large molecule antibiotics, protein based thrombolytic compounds, platelet inhibitors, DNA, RNA, gene therapeutics, antisense oligonucleotides, opioids, narcotics, hypnotics, steroids and pain killers.

The present invention also provides a process for making a pharmaceutical composition suitable for delivery through transdermal membranes comprising the steps of:

a) mixing a proteinic pharmaceutical agent composition in an aqueous medium with an alkali metal C8 to C22 alkyl sulphate, and at least one micelle forming compound selected from the group consisting of lecithin, hyaluronic acid, pharmaceutically acceptable salts of hyaluronic acid, glycolic acid, lactic acid, chamomile extract, cucumber extract, oleic acid, linoleic acid, linolenic acid, monoolein, monooleates, monolaurates, borage oil, evening of primrose oil, menthol, trihydroxy oxo cholanyl glycine and pharmaceutically acceptable salts thereof, glycerin, polyglycerin, lysine, polylysine, triolein, polyoxyethylene ethers and analogues thereof, polidocanol alkyl ethers and analogues thereof, and mixtures thereof, to form a micellar proteinic pharmaceutical agent composition;

b) during step a) or after step a), adding at least one micelle forming compound, different from that added in step a);

c) during step a) or after step a), adding a phenolic compound selected from the group consisting of phenol, m-cresol and mixtures thereof; and subsequently d) placing the formulation into an aerosol dispenser and charging the dispenser a propellant;

wherein the composition has at least three micelle forming compounds and the amount of the micelle forming compounds are each present in a concentration of from 1 to 20 wt./wt. % of the total formulation, and the total concentration of alkali metal alkyl sulphate and micelle forming compounds is less than 50 wt./wt. % of the formulation.

In one embodiment, the process comprises:

a') mixing the proteinic pharmaceutical agent composition in an aqueous medium with the alkali metal C8 to C22 alkyl sulphate and optionally at least one of the micelle forming compounds, to form a micellar proteinic pharmaceutical agent composition;

b') slowly adding at least one of the micelle forming compounds, different from that added in step a'), while mixing vigorously, to form a mixed micellar composition;

c') mixing the mixed micellar composition resulting from steps a') and b') with the phenolic compound; and subsequently d') placing the formulation into an aerosol dispenser and charging the dispenser a propellant.

In another embodiment, the process comprises the steps of:

a") mixing the proteinic pharmaceutical agent composition in an aqueous medium with the alkali metal C8 to C22 alkyl sulphate and optionally at least one of the micelle forming compounds, while mixing vigorously, to form a mixed micellar composition;

b") mixing the mixed micellar composition resulting from step a") with the phenolic compound; and subsequently c") placing the formulation into an aerosol dispenser and charging the dispenser a propellant.

In a further embodiment, the alkali metal alkyl sulphate is sodium lauryl sulphate.

In yet another embodiment, the formulation has micelle forming compound combinations selected from the group consisting of sodium hyaluronate, monoolein and saturated phospholipid, ii) saturated phospholipid, monoolein and glycolic acid, iii) sodium hyaluronate, polyoxyethylene ether and lecithin, iv) polyoxyethylene ether, trihydroxy oxo cholanyl and lecithin, v) polidocanol 9 lauryl ether, polylysine and triolein, and vi) saturated phospholipid, polyoxyethylene ether and glycolic acid The vigorous mixing may be accomplished by using high speed stirrers, e.g. magnetic stirrers or propellor stirrers, or by sonication.

In one embodiment, the mixed micellar formulation is formed by sonication of the aqueous micellar pharmaceutical agent composition in which one of the micelle forming compounds is lecithin.

The present invention also provides a metered dose aerosol dispenser with the composition of the present invention therein, in which an aqueous phase containing the proteinic pharmaceutical agent is substantially separated from a phase containing the propellant.

The present invention also provides a method for administering mixed micellar pharmaceutical formulations of the present invention, by means of shaking the aerosol dispenser in order to intermix the aqueous and propellant phases, and then spraying the intermixed composition into the mouth with a metered dose spray device.

DETAILED DESCRIPTION OF PREFERRED EMBODIMENTS

The present invention provides an improved method for delivery of macromolecular (high molecular weight) pharmaceutical agents, particularly through the membranes in the mouth or lungs. The pharmaceutical agents cover a wide spectrum of agents, including proteins, peptides, hormones, vaccines and drugs. The molecular weights of the macromolecular pharmaceutical agents are preferably above 1000, especially between 1000 and 2,000,000.

For example, hormones which may be administered with the present invention include thyroids, androgens, estrogens, prostaglandins, somatotropins, gonadotropins, erythropoetin, interferons, interleukins, steroids and cytokines. Vaccines which may be administered with the present invention include bacterial and viral vaccines such as vaccines for hepatitis, influenza, tuberculosis, canary pox, chicken pox, measles, mumps, rubella, pneumonia, BCG, HIV and AIDS. Bacterial toxoids which may be administered using the present invention include diphtheria, tetanus, pseudomonas and mycobactrium tuberculosis. Examples of specific cardiovascular or thrombolytic agents include heparin, hirugen, hirulos and hirudine. Large molecules usefully administered with the present invention include monoclonal antibodies, polyclonal antibodies and immunoglobins.

As will be understood, the concentration of the pharmaceutical agent is an amount sufficient to be effective in treating or preventing a disorder or to regulate a physiological condition in an animal or human. The concentration or amount of pharmaceutical agent administered will depend on the parameters determined for the agent and the method of administration, e.g. nasal, buccal, pulmonary. For example, nasal formulations tend to require much lower concentrations of some ingredients in order to avoid irritation or burning of the nasal passages. It is sometimes desirable to dilute an oral formulation up to 10–100 times in order to provide a suitable nasal formulation.

The mixed micellar formulation may be prepared by mixing an aqueous solution of the pharmaceutical agent, the alkali metal C8 to C22 alkyl sulphate, at least three micelle forming compounds, and optionally the phenolic compound. The micelle forming compounds may be added at the same time or after addition of the alkali metal alkyl sulphate.

Mixed micelles will form with substantially any kind of mixing of the ingredients but vigorous mixing is preferred in order to provide smaller size micelles.

In one method a first micellar composition is prepared which contains the pharmaceutically active agent and at least the alkali metal alkyl sulphate. The first micellar composition is then mixed with at least three micelle forming compounds to form a mixed micellar composition. In another method, the micellar composition is prepared by mixing the pharmaceutically active agent, the alkali metal alkyl sulphate and at least one of the micelle forming compounds, followed by addition of the remaining micelle forming compounds, with vigorous mixing.

The phenol and/or m-cresol may be added to the mixed micellar composition to stabilize the formulation and protect against bacterial growth. Alternatively, the phenol and/or m-cresol may be added with the micelle forming ingredients. An isotonic agent such as glycerin may also be added after formation of the mixed micellar composition. The formulation is then put into an aerosol dispenser and the dispenser charged with the propellant. The propellant, which is under pressure, is in liquid form in the dispenser. In the present invention, when the composition of the present invention is in a dispenser, the aqueous phase is separated from the propellant phase. Because there are two phases, it is necessary to shake the dispenser prior to dispensing a portion of the contents, e.g. through a metered valve. The dispensed dose of pharmaceutical agent is propelled from the metered valve in a fine spray.

The preferred propellants are hydrogen-containing chlorofluorocarbons, hydrogen-containing fluorocarbons, dimethyl ether and diethyl ether. Even more preferred is HFA 134a (1,1,1,2 tetrafluoroethane).

Although the present invention has such wide applicability, the invention is described hereinafter with particular reference to insulin and its analogues, which are used for the treatment of diabetes.

As indicated hereinbefore, the aerosol compositions of the present invention require that the pharmaceutical formulation be in mixed micellar form.

In the case of insulin, which is intended for administration through the mouth cavity, the first micellar solution may be made by adding water, and then hydrochloric acid (typically 5M) to powdered insulin, and then stirring until the powder is dissolved and a clear solution is obtained. The solution is then neutralized with sodium hydroxide. The sodium alkyl sulphate is added with low speed stirring, either alone or with at least one micelle forming compound. A typical concentration of sodium lauryl sulphate, as the sodium alkyl sulphate, in the aqueous solution is about 3 to 20 wt./wt. % of the solution. Typically, insulin is present in the micellar solution in an amount which will give a concentration of about 2 to 4 wt./wt. % of the final formulation.

The micellar solution so formed may then be mixed vigorously, e.g. by sonication or high speed stirring, to form a mixed micelle liposomal solution. Other micelle forming compounds may then be added. For example, one or more micelle forming compounds selected from the group consisting of lecithin, hyaluronic acid, pharmaceutically acceptable salts of hyaluronic acid, glycolic acid, lactic acid, chamomile extract, cucumber extract, oleic acid, linoleic acid, linolenic acid, monoolein, monooleates, monolaurates, borage oil, evening of primrose oil, menthol, trihydroxy oxo cholanyl glycine and pharmaceutically acceptable salts thereof, glycerin, polyglycerin, lysine, polylysine, triolein, polyoxyethylene ethers and analogues thereof, polidocanol alkyl ethers and analogues thereof may be added. The mixing may be done with a high speed mixer or sonicator to ensure uniform micelle particle size distribution within the formulation.

After forming the mixed micellar formulation, the phenol and/or m-cresol is added prior to charging the composition to an aerosol dispenser. As indicated above, other ingredients, such as isotonic agents, flavouring agents, antioxidants, salts, protease inhibitors or other pharmaceutically acceptable compounds may also be added. After the formulation is in the aerosol dispenser, the dispenser is charged with propellant in a known manner.

Each of the micelle forming compounds, when present, is in a concentration of from 1 to 20 wt./wt. % of the total formulation.

Preferred salts of hyaluronic acid are alkali metal hyaluronates, alkaline earth hyaluronates and aluminium hyaluronate. The preferred salt is sodium hyaluronate. The preferred concentration of hyaluronic acid or pharmaceutically acceptable salts of hyaluronic acid is from 1 to 5 wt./wt. % of the total formulation. An even more preferred range is from 1.5 to 3.5 wt./wt. % of the total formulation.

The specific concentrations of the essential ingredients can be determined by relatively straightforward experimentation. It will be understood that the amounts of certain ingredients may need to be limited in order to avoid compositions which produce foam when sprayed rather than forming a fine spray. For absorption through the oral cavities, it is often desirable to increase, e.g. double or triple, the dosage which is normally required through injection or administration through the gastrointestinal tract.

As will be understood, the amount of each component of the formulation will vary depending on the pharmaceutical agent and the site of application. Preferred formulations buccal application have the following combinations: i) sodium lauryl sulphate, polidocanol 10 lauryl ether, sodium oxo cholanyl glycine and lecithin; ii) sodium lauryl sulphate, polidocanol 10 lauryl ether, phosphatidyl choline, oleic acid; iii) sodium lauryl sulphate, polidocanol 10 lauryl ether, sodium hyaluronate and lecithin; iv) sodium lauryl sulphate, polidocanol 9 lauryl ether, triolein and polylysine; v) sodium lauryl sulphate, polyoxyethylene ether (10 lauryl), trihydroxy oxo cholanyl glycine and lecithin, and vi) sodium lauryl sulphate, polidocanol 20 lauryl ether, evening of primrose oil and lecithin.

The therapeutic compositions of the present invention may be stored at room temperature or at cold temperature. Storage of proteinic drugs is preferable at a cold temperature to prevent degradation of the drugs and to extend their shelf life.

It is believed that the mixed micelles of the present invention encapsulate molecules with a high degree of efficiency (>90% encapsulation). In general the size of the micelle particles in the mixed micellar composition is about 1 to 10 nm or less, and preferably from 1 to 5 nm. Such mixed micelles tend to be smaller than the pores of the membranes in the oral cavity or the GI tract. It is therefore believed that the extremely small size of mixed micelles helps the encapsulated molecules penetrate efficiently through the mucosal membranes of the oral cavity.

The desired size of aerosol droplets which are sprayed from the aerosol dispenser will depend, in part, on where the pharmaceutical is to be deposited. For example, for deposition in the lungs, particle sizes of less than about 5 µm are preferred whereas for absorption in the buccal cavity of the mouth, particle sizes of about 6–10 µm are preferred.

The amount of physiologically peptide or protein in the compositions of this invention is typically a quantity that provides an effective amount of the pharmaceutical or drug to produce the physiological activity (therapeutic plasma level) for which peptide or protein is being administered. In consideration of the fact that the bioavailability of any active substance can never be 100%, that is to say the administered dose of the active drug is not completely absorbed, it is preferable to incorporate slightly larger amount than the desired dosage.

It is believed that improvements in penetration and absorption of mixed micellar formulations are achieved by mixing the mixed micellar formulation with propellants such as tetrafluoroethane, heptafluoroethane, dimethylfluoropropane, tetrafluoropropane, butane, isobutane, dimethyl ether and other non-CFC and CFC propellants. Preferably they are delivered through metered dose spray devices. Metered dose inhalers are known and are a popular pulmonary drug delivery form for some drugs. One of the benefits of using an atomizer or inhaler is that the potential for contamination is minimized because the devices are self contained.

The present formulation, including the propellant, is intended to improve the quality of absorption, stability and performance of many formulations. The compositions have been selected to give enhancement in the penetration through pores, and facilitate absorption of the drugs to reach therapeutic levels in the plasma.

Administration of the formulation into the buccal cavity is by spraying the formulation into the mouth, without inhalation, so that the droplets stay in the mouth rather than be drawn into the lungs.

The invention is illustrated by reference to the following examples.

EXAMPLE 1

A first experiment was conducted to provide data for comparative purposes. This example does not fall within the scope of the present invention.

Powdered insulin was placed in a glass beaker equipped with a stirrer. Distilled water was added and the solution was stirred at low speed. To this solution was added 5M HCl (pH 2) solution dropwise until the insulin was solubilized completely. This solution was then neutralized with 5M NaOH solution dropwise until the pH was between 7 and 8. Seven mg phenol and 7 mg m-cresol were added to the solution and mixed thoroughly.

The solution was diluted with distilled water until there were 200 units insulin per millilitre of solution.

One millilitre portions were then transferred to glass vials, which were then charged with 10.8 g HFA 134a propellant using a Pamasol (trade mark) 2008 semi-automatic gas filling apparatus.

Ten diabetic volunteers were asked to fast overnight and not have any breakfast prior to dosing. On the first day, the volunteers were given 10 units insulin by injection (regular fast acting insulin, available from Eli Lilly). On the second day, the volunteers were given 60 units insulin of this example (10 puffs of 6 units each) into the mouth, without inhalation. Blood glucose levels were monitored at intervals using Bayer's glucometer Elite for 3 hours. The average results, in millimoles per litre, are shown in Table I.

TABLE I

| Time*: | 0 | 15 | 30 | 60 | 90 | 120 | 150 | 180 |
|---|---|---|---|---|---|---|---|---|
| Injection: | 6.8 | 6.6 | 5.9 | 5.3 | 4.9 | 4.5 | 4.1 | 3.7 |
| Spray: | 6.3 | 6.8 | 6.2 | 6.8 | 6.1 | 6.7 | 6.5 | 6.2 |

*time in minutes

These tests indicate that compared to the injection method, the spray method with formulations without the alkali metal alkyl sulphate and absorption enhancers of the present invention failed to lower the blood glucose levels in diabetic patients. Thus, combination of the formulation and the spray method of application had no metabolic effect.

EXAMPLE 2

Powdered insulin was placed in a glass beaker equipped with a stirrer. Distilled water was added and the solution was stirred at low speed. To this solution was added 5M HCl (pH 2) solution dropwise until the insulin was solubilized completely. This solution was then neutralized, while stirring slowly, with 5M NaOH solution dropwise until the pH was between 7 and 8. To this solution was added 7 mg sodium lauryl sulphate, 7 mg polyoxyethylene ether (10 lauryl) and 7 mg trihydroxy oxo cholanyl glycine and dissolved completely. Seven mg lecithin, solubilized in a water alcohol solution (7 mg/mL) was then added while stirring at high speed, i.e. 2000 rpm. The solution was stirred for 30 minutes and then stored at 10° C. The resulting mixed micellar solution had about 200 units insulin. To this mixture 5 mg phenol, 5 mg m-cresol and 10 mg glycerin were added.

The solution was pipetted (1mL/vial) into 10 mL capacity glass vials. The vials were then charged with HFA 134a propellant with a Pamasol 2008 automatic gas filling apparatus. The amount of propellant was adjusted to 9 mL shot size in order to deliver 2 units insulin per actuation of the aerosol vial. The valves of the vials were designed to deliver 100 μL spray per actuation, containing 2 units insulin.

The aerodynamic particle size was determined by an 8-stage USP Anderson (trade mark) Cascade Impactor Mark II. The impactor was cleaned with methanol and air dried at 30° C. Glass fibre filters were placed on the collection plates. The actuator was attached to the mouthpiece of the impactor and assembled onto the USP induction port and jet stages. A vacuum pump was connected and the air flow rate set to 28.3 litres per minute. The vial was primed by shaking for 10 seconds and actuating twice to waste. The shot was delivered by discharging the actuator into the mouthpiece and repeating 25 times. The deposited insulin was collected by rinsing the mouthpiece with 0.6 mL EDTA in 10 mL water at pH 8.7. The filters were removed and placed in scintillation vials and sonicated for 15 minutes. The quantity of insulin was then analysed using RP-HPLC. The results are shown in Table II (2 units per actuation) and III (4 units per actuation).

TABLE II

| Stage No. | 0 | 1 | 2 | 3 |
|---|---|---|---|---|
| Volume (mL) | 10 | 10 | 10 | 10 |
| Mass (mg) | 0.79 | 0.81 | 0.78 | * |
| Units | 10.4 | 10.0 | 10.0 | |
| Actuation | 5 | 5 | 5 | |

TABLE II-continued

| Stage No. | 0 | 1 | 2 | 3 |
|---|---|---|---|---|
| Units per actuation | 2.0 | 2.0 | 2.1 | |
| Particle size (μm) | 8.8 | 5.8 | 5.7 | |

* not determined/detected

TABLE III

| Stage No. | 0 | 1 | 2 | 3 |
|---|---|---|---|---|
| Volume (mL) | 10 | 10 | 10 | 10 |
| Mass (mg) | | 0.79 | 0.81 | 0.78 | ** |
| Units | | 20.7 | 21.0 | 20.1 | |
| Actuation | | 5 | 5 | 5 | |
| Units per actuation | | 4.15 | 4.18 | 4.01 | |
| Particle size (μm) | | 9 | 5.8 | 4.7 | |

** not determined

Based on these tests, the particle size was determined to be about 7 μm, and stages 3–8 showed no insulin deposition, indicating that most particles were larger than about 6 μm. This suggests that there would be no deep lung deposition formulation and that most of the formulation would be deposited in the buccal cavity.

Further tests were conducted to determine the shot size accuracy, by firing shots into thiel tubes and weighing the tubes before and after the sample collection. The tests showed the shots for 2 units per actuation weighed between 0.075 and 0.083 grams, i.e within about ±5%. The tests showed the shots for 4 units per actuation weighed between 0.076 and 0.083 grams, i.e within about ±5%. The tests showed the shots for 6 units per actuation weighed between 0.070 and 0.082 grams, i.e within about ±8%. HPLC analysis showed the doses delivered to be from 2.01 units to 2.07 units for 2 units per actuation, from 3.9 units to 4.4 units for 4 units per actuation, and from 5.8 units to 6.3 units for 6 units per actuation.

Ten diabetic volunteers were asked to fast overnight and not have any breakfast prior to dosing. On the first day, the volunteers were given 10 units insulin by injection (regular fast acting insulin, available from Eli Lilly). On the second day, the volunteers were given 60 units insulin of this example (10 puffs of 6 units each) into the mouth, without inhalation. Plasma insulin levels were measured at intervals by the RIA method for 3 hours. The average results, in micromoles per millilitre, are shown in Table IV. Blood glucose levels were also monitored at intervals using Bayer's glucometer Elite for 3 hours.

The average results, in millimoles per litre, are shown in Table V.

TABLE IV

| Time*: | 0 | 15 | 30 | 45 | 60 | 90 | 120 | 150 | 180 |
|---|---|---|---|---|---|---|---|---|---|
| Injection: | 10 | 9.1 | 11 | 16 | 31 | 45 | 32 | 25 | 20 |
| Spray: | | 8.7 | 12.1 | 19.8 | 28 | 27 | 36 | 29 | 21 | 13 |

*time in minutes

This test indicated that the injection method and spray method were comparable.

TABLE V

| Time*: | 0 | 15 | 30 | 45 | 60 | 90 | 120 | 150 | 180 |
|---|---|---|---|---|---|---|---|---|---|
| Injection: | 6.1 | 6.0 | 5.9 | 5.5 | 5.1 | 4.5 | 3.8 | 4.2 | 4.4 |
| Spray: | 6.6 | 6.3 | 5.8 | 5.2 | 4.8 | 4.9 | 4.5 | 5.0 | 5.3 |

*time in minutes

This test indicated that the injection method and spray method were comparable in terms of glucose level.

Tests were also conducted with 40 units of spray at 10 puffs each, and compared to 10 units injected by measuring plasma levels and glucose levels as above. The results are shown in Table VI (plasma) and VII (glucose).

TABLE VI

| Time*: | 0 | 15 | 30 | 45 | 60 | 90 | 120 | 150 | 180 |
|---|---|---|---|---|---|---|---|---|---|
| Injection: | 9 | 9 | 13 | 19 | 34 | 45 | 42 | 35 | 24 |
| Spray: | 10 | 13 | 18.5 | 27 | 30 | 33 | 29 | 19 | 14 |

*time in minutes

This test indicated that the injection method and spray method were comparable in terms of plasma insulin levels.

TABLE VI

| Time*: | 0 | 15 | 30 | 60 | 90 | 120 | 150 | 180 |
|---|---|---|---|---|---|---|---|---|
| Injection: | 5.8 | 6.0 | 5.9 | 5.5 | 5.0 | 4.5 | 4.1 | 3.9 |
| Spray: | 6.0 | 5.7 | 5.4 | 5.0 | 5.1 | 4.7 | 4.5 | 4.2 |

*time in minutes

This test indicated that the injection method and spray method were comparable in terms of glucose levels.

EXAMPLE 3

Powdered insulin was placed in a glass beaker equipped with a stirrer. Distilled water was added and the solution was stirred at low speed. To this solution was added 5M HCl (pH 2) solution dropwise until the insulin was solubilized completely. This solution was then neutralized, while stirring slowly, with 5M NaOH solution dropwise until the pH was between 7 and 8. To this solution was added 30.4 mg sodium lauryl sulphate per millilitre of insulin solution, 30.4 mg polidocanol 9 lauryl ether per millilitre of insulin solution and 10.0 mg polylysine per millilitre of insulin solution, and dissolved completely. 15.2 mg triolein per millilitre of insulin solution was then added while stirring at high speed, i.e. 2000 rpm. The solution was stirred for 30 minutes and then stored at 10° C. The resulting solution was a mixed micellar solution. To this mixture 15.2 mg m-cresol per millilitre of insulin solution were added.

The solution was pipetted (1 mL) into glass vials. The vials were then charged with 10.8 g HFA 134a propellant per vial, with a Pamasol 2008 automatic gas filling apparatus. The valves of the vials were designed to deliver 100 μL spray per actuation, containing 6 units insulin.

Ten diabetic volunteers were asked to fast overnight and not have any breakfast prior to dosing.

On the first day, the volunteers were given 10 units insulin by injection (regular fast acting insulin, available from Eli Lilly). On the second day, the volunteers were given 60 units insulin of this example (10 puffs of 6 units each) into the mouth, without inhalation. Plasma insulin levels were measured at intervals by the RIA method for 3 hours. The average results, in micromoles per millilitre, are shown in Table VII. Blood glucose levels were also monitored at intervals using Bayer's glucometer Elite for 3 hours. The average results, in millimoles per litre, are shown in Table VIII.

TABLE VII

| Time*: | 0 | 15 | 30 | 45 | 60 | 90 | 120 | 150 | 180 |
|---|---|---|---|---|---|---|---|---|---|
| Injection: | 9 | 9.1 | 14 | 20 | 40 | 48 | 39 | 34 | 27 |
| Spray: | 10 | 15.1 | 22 | 32 | 47 | 36 | 27 | 21 | 19 |

*time in minutes

This test indicated that the injection method and spray method were comparable.

TABLE VIII

| Time*: | 0 | 15 | 30 | 45 | 60 | 90 | 120 | 150 | 180 |
|---|---|---|---|---|---|---|---|---|---|
| Injection: | 6.6 | 6.5 | 6.1 | 5.5 | 4.9 | 4.5 | 3.8 | 3.5 | 4.4 |
| Spray: | 6.8 | 5.9 | 5.2 | 4.8 | 4.3 | 3.9 | 4.5 | 5.7 | 5.3 |

*time in minutes

This test indicated that the injection method and spray method were comparable in terms of glucose level.

EXAMPLE 4

A further experiment was conducted to provide data for comparative purposes.

Powdered insulin was placed in a glass beaker equipped with a stirrer. Distilled water was added and the solution was stirred at low speed. To this solution was added 5M HCl (pH 2) solution dropwise until the insulin was solubilized completely. This solution was then neutralized with 5M NaOH solution dropwise until the pH was between 7 and 8. The solution was diluted with distilled water until there were 600 units insulin per millilitre of solution. One millilitre portions were then transferred to 10 mL capacity glass vials, which were then charged with 10.8 g HFA 134a propellant using a Pamasol (trade mark) 2008 semi-automatic gas filling apparatus. This formulation does not fall within the scope of the present invention.

The gas phase and the aqueous phase were observed to be distinctly separate. Even shaking of the vials did not appear to homogenize the composition.

Tests were conducted to determine the shot size accuracy, by firing shots into thiel tubes and weighing the tubes before and after the sample collection. The tests showed five consecutive shots for 6 units per actuation weighed 0.094, 0.110, 0.200, 0.150 and 0.050 grams, i.e within about ±60% of the average. This compares with ±8% in Example 2 (which is within the scope of the present invention).

HPLC analysis showed the average doses delivered to be 5.4 units per actuation from shots 5–10, 7.1 units per actuation from shots 45–50 and 8.6 units per actuation from shots 85–90.

These results showed that such composition, without the micelle-forming ingredients, gave non-uniform dose delivery.

What is claimed is:

1. A mixed micellar aerosol pharmaceutical formulation comprising i) a pharmaceutical agent in micellar form, ii) water, iii) an alkali metal C8 to C22 alkyl sulphate in a concentration of from 1 to 20 wt./wt. % of the total formulation, iv) at least three micelle forming compounds selected from the group consisting of lecithin, hyaluronic acid, pharmaceutically acceptable salts of hyaluronic acid, glycolic acid, lactic acid, chamomile extract, cucumber extract, oleic acid, linoleic acid, linolenic acid, monoolein, monooleates, monolaurates, borage oil, evening of primrose oil, menthol, trihydroxy oxo cholanyl glycine and pharmaceutically acceptable salts thereof, glycerin, polyglycerin, lysine, polylysine, triolein, polyoxyethylene ethers, polidocanol alkyl ethers, and mixtures thereof, wherein the amount of each micelle forming compound is present in a concentration of from 1 to 20 wt./wt. % of the total formulation, and the total concentration of micelle forming compounds are less than 50 wt./wt. % of the formulation, v) a phenolic compound selected from the group consisting of phenol and methyl phenol in a concentration of from 1 to 10 wt./wt. % of the total formulation, and vi) a propellant selected from the group consisting of C1–C2 dialkyl ether, butanes, fluorocarbon propellant, hydrogen-containing fluorocarbon propellant, chlorofluorocarbon propellant, hydrogen-containing chlorofluorocarbon propellant, and mixtures thereof, said pharmaceutical formulation having a pharmaceutically acceptable pH.

2. A formulation according to claim 1 wherein the alkali metal C8 to C22 alkyl sulphate is in a concentration of from 2 to 5 wt./wt. % of the total formulation.

3. A formulation according to claim 2 wherein the alkali metal C8 to C22 alkyl sulphate is sodium lauryl sulphate.

4. A formulation according to claim 2 wherein the propellant is selected from the group consisting of tetrafluoroethane, tetrafluoropropane, dimethylfluoropropane, heptafluoropropane, dimethyl ether, n-butane and isobutane.

5. A formulation according to claim 2 wherein the pharmaceutical agent is insulin.

6. A formulation according to claim 1 wherein the alkali metal C8 to C22 alkyl sulphate is sodium lauryl sulphate.

7. A formulation according to claim 1 wherein the lecithin selected from the group consisting of saturated phosphatidylcholine, unsaturated phosphatidylcholine, phosphatidyl serine, sphingomyelin, phosphatidylethanolamine, cephalin, and lysolecithin.

8. A formulation according to claim 1 wherein one of the micelle forming compounds is selected from the group consisting of hyaluronic acid, pharmaceuticaly acceptable salts of hyaluronic acid, polidocanol alkyl ethers, trihydroxy oxo cholanyl glycine and pharmaceutically acceptable salts thereof, polyoxyethylene ethers and mixtures thereof, the concentration of such micelle forming compound being from about 1 to 5 wt./wt. %.

9. A formulation according to claim 1 wherein the propellant is selected from the group consisting of tetrafluoroethane, tetrafluoropropane, dimethylfluoropropane, heptafluoropropane, dimethyl ether, n-butane and isobutane.

10. A formulation according to claim 1 wherein the formulation comprises combinations selected from the group consisting of i) sodium lauryl sulphate, polidocanol 10 lauryl ether, sodium oxo cholanyl glycine and lecithin; ii) sodium lauryl sulphate, polidocanol 10 lauryl ether, sodium hyaluronate and lecithin; iii) sodium lauryl sulphate, polidocanol 9 lauryl ether, triolein and polylysine; iv) sodium lauryl sulphate, polyoxyethylene ether (10 lauryl), trihydroxy oxo cholanyl glycine and lecithin, and v) sodium lauryl sulphate, polidocanol 20 lauryl ether, evening of primrose oil and lecithin.

11. A formulation according to claim 1 wherein the pharmaceutical agents are selected from the group consisting of insulin, heparin, low molecular weight heparin, hirulog, hirugen, huridine, interferons, interleukins, cytokines, mono and polyclonal antibodies, immunoglobins, chemotherapeutic agents, vaccines, glycoproteins, bacterial toxoids, hormones, calcitonins, insulin like growth factors (IGF), glucagon like peptides (GLP-1), large molecule antibiotics, protein based thrombolytic compounds, platelet inhibitors, DNA, RNA, gene therapeutics, antisense oligonucleotides, opioids, narcotics, hypnotics, steroids and pain killers.

12. A formulation according to claim 1 wherein the ratio of proteinic pharmaceutical agent to propellant is from 5:95 to 25:75.

13. A formulation according to claim 1 which is contained in a metered dose device.

14. A formulation according to claim 1 wherein the formulation comprises sodium lauryl sulphate, polidocanol 10 lauryl ether, phosphatidyl choline and oleic acid.

15. A process for making a pharmaceutical composition suitable for delivery through mucosal membranes comprising the steps of:
   a) mixing a pharmaceutical agent composition in an aqueous medium with an alkali metal C8 to C22 alkyl sulphate, and at least one micelle forming compound selected from the group consisting of lecithin, hyaluronic acid, pharmaceutically acceptable salts of hyaluronic acid, glycolic acid, lactic acid, chamomile extract, cucumber extract, oleic acid, linoleic acid, linolenic acid, monoolein, monooleates, monolaurates, borage oil, evening of primrose oil, menthol, trihydroxy oxo cholanyl glycine and pharmaceutically acceptable salts thereof, glycerin, polyglycerin, lysine, polylysine, triolein, polyoxyethylene ethers, polidocanol alkyl ethers, and mixtures thereof, to form a micellar pharmaceutical agent composition;
   b) during step a) or after step a), adding at least one micelle forming compound, different from that added in step a) and adjusting the pH to a pharmaceutically acceptable level;
   c) during step a) or after step a), adding a phenolic compound in an amount of 1–10 wt./wt. % of the total formulation and selected from the group consisting of phenol, m-cresol and mixtures thereof, and subsequently
   d) placing the formulation into an aerosol dispenser and charging the dispenser a propellant selected from the group consisting of $C_1$–$C_2$ diakyl ether, butanes, fluorocarbon propellant, hydrogen-containing fluorocarbon propellant, chlorofluorocarbon propellant, hydrogen-containing chlorofluorocarbon propellant and mixtures thereof,
   wherein the composition has at least three micelle forming compounds and the amount of the micelle forming compounds are each present in a concentration of from 1 to 20 wt./wt. % of the total formulation, and the total concentration of alkali metal alkyl sulphate and micelle forming compounds is less than 50 wt./wt. % of the formulation.

16. A process according to claim 15 wherein the alkali metal alkyl sulphate is sodium lauryl sulphate.

17. A process according to claim 15 wherein the propellant is selected from the group consisting of tetrafluoroethane, tetrafluoropropane, dimethylfluoropropane, heptafluoropropane, dimethyl ether, n-butane and isobutane.

18. A process according to claim 15 wherein the formulation comprises combinations selected from the group consisting of i) sodium lauryl sulphate, polidocanol 10 lauryl ether, sodium oxo cholanyl glycine and lecithin; ii) sodium lauryl sulphate, polidocanol 10 lauryl ether, phosphatidyl choline, oleic acid; iii) sodium lauryl sulphate, polidocanol 10 lauryl ether, sodium hyaluronate and lecithin; iv) sodium lauryl sulphate, polidocanol 9 lauryl ether, triolein and polylysine; v) sodium lauryl sulphate, polyoxyethylene ether (10 lauryl), trihydroxy oxo cholanyl glycine and lecithin, and vi) sodium lauryl sulphate, polidocanol 20 lauryl ether, evening of primrose oil and lecithin.

19. A process according to claim 15 wherein the pharmaceutical agent is selected from the group consisting of insulin, heparin, low molecular weight heparin, hirulog, hirugen, huridine, interferons, interleukins, cytokines, mono and polyclonal antibodies, immunoglobins, chemotherapeutic agents, vaccines, glycoproteins, bacterial toxoids, hormones, calcitonins, insulin like growth factors (IGF), glucagon like peptides (GLP-1), large molecule antibiotics, protein based thrombolytic compounds, platelet inhibitors, DNA, RNA, gene therapeutics, antisense oligonucleotides, opioids, narcotics, hypnotics, steroids and pain killers.

20. A method of administering a mixed micellar aerosol pharmaceutical formulation comprising i) a pharmaceutical agent in micellar form, ii) water, iii) an alkali metal C8 to C22 alkyl sulphate in a concentration of from 1 to 20 wt./wt. % of the total formulation, iv) at least three micelle forming compounds selected from the group consisting of lecithin, hyaluronic acid, pharmaceutically acceptable salts of hyaluronic acid, glycolic acid, lactic acid, chamomile extract, cucumber extract, oleic acid, linoleic acid, linolenic acid, monoolein, monooleates, monolaurates, borage oil, evening of primrose oil, menthol, trihydroxy oxo cholanyl glycine and pharmaceutically acceptable salts thereof, glycerin, polyglycerin, lysine, polylysine, triolein, polyoxyethylene ethers, polidocanol alkyl ethers, and mixtures thereof, wherein the amount of each micelle forming compound is present in a concentration of from 1 to 20 wt./wt. % of the total formulation, and the total concentration of micelle forming compounds are less than 50 wt./wt. % of the formulation, v) a phenolic compound selected from the group consisting of phenol and methyl phenol in a concentration of from 1 to 10 wt./wt./% of the total formulation, and vi) a propellant selected from the group consisting of C1–C2 dialkyl ether, butanes, fluorocarbon propellant, hydrogen-containing fluorocarbon propellant, chlorofluorocarbon propellant, hydrogen-containing chlorofluorocarbon propellant, and mixtures thereof, said formulation having a pharmaceutically acceptable pH, in which the formulation is administered from an aerosol into a mouth of a person to be treated.

* * * * *